| United States Patent [19] | [11] | Patent Number: | 4,467,121 |
|---|---|---|---|
| Mark et al. | [45] | Date of Patent: | Aug. 21, 1984 |

[54] FLUORINATED DIPHENOLS AND METHOD FOR THEIR PREPARATION

[75] Inventors: Victor Mark, Evansville; Charles V. Hedges, Mount Vernon, both of Ind.

[73] Assignee: General Electric Company, Mt. Vernon, Ind.

[21] Appl. No.: 402,165

[22] Filed: Jul. 26, 1982

Related U.S. Application Data

[62] Division of Ser. No. 221,884, Dec. 31, 1980, Pat. No. 4,365,098.

[51] Int. Cl.$^3$ .............................................. C07C 39/16
[52] U.S. Cl. .................................... 568/726; 568/727; 568/775
[58] Field of Search ........................ 568/726, 727, 728

[56] References Cited

U.S. PATENT DOCUMENTS

| 2,734,088 | 2/1956 | Knowles et al. | |
|---|---|---|---|
| 3,340,310 | 9/1967 | Gilbert et al. | 568/726 |
| 3,388,097 | 6/1968 | Cramer | 568/726 |
| 4,358,624 | 11/1982 | Mark et al. | 568/726 |
| 4,365,098 | 12/1982 | Mark et al. | 568/726 |

FOREIGN PATENT DOCUMENTS

| 1263513 | 5/1961 | France. | |
|---|---|---|---|
| 1017988 | 1/1966 | United Kingdom | 568/726 |
| 1029750 | 5/1966 | United Kingdom | 568/726 |
| 1095959 | 12/1967 | United Kingdom | 568/726 |
| 1459420 | 12/1976 | United Kingdom. | |

OTHER PUBLICATIONS

"Gevaert-Photo Producten", French Patent Abstract, Pharmaceuticals Photographic' French, 5/21/65.
Korshal et al., "Chem. Abstract", vol. 64, (1966), pp. 67663 and 8321h.

*Primary Examiner*—Werren B. Lone
*Attorney, Agent, or Firm*—Martin B. Barancik

[57] ABSTRACT

Fluorinated bisphenols having a fluorinated alkyl group and a hydrogen atom upon the methylene carbon atom are prepared at atmospheric pressure or at low pressures from a phenol reactant and a fluorinated aldehyde compound in the presence of gaseous hydrogen chloride or gaseous hydrogen bromide catalyst. The fluorinated bisphenols having the fluorinated alkyl group and a hydrogen atom upon the methylene carbon atom are produced in excellent yields and are used for making flame-retardant polycarbonates and polyester-carbonate copolymers.

10 Claims, No Drawings

FLUORINATED DIPHENOLS AND METHOD FOR THEIR PREPARATION

This is a division of copending application Ser. No. 221,884, filed Dec. 31, 1980, now U.S. Pat. No. 4,365,098.

This invention relates to an improved method of making diphenols having fluorinated alkyl groups and the compositions made therefrom, and more particularly, to an improved method of making diphenols having a fluorinated alkyl group and a hydrogen atom upon the methylene carbon atom.

BACKGROUND OF THE INVENTION

Diphenols, otherwise known as bisphenols, are well-known in the art and are commonly used in the preparation of polycarbonates, polyesters, polyester-carbonate copolymers and other polymers and copolymers. It is well-known that by varying the structures of the monomers used to make the foregoing polymers and copolymers, substantial changes in various properties can be realized, such as changes in impact strength, toughness, transparency, heat distortion limits, dimensional stability, creep resistance, flame-retardancy and the like. It is also desirable to improve such properties, where possible, by changing or altering the structure of monomers used in the polymers or copolymers, and accordingly, it is desirable to provide new and improved monomers to improve the properties of the resultant polymers. Polycarbonate compositions having improved flame-retardance are disclosed in U.S. Pat. No. 4,182,838 where halogenated vinylidene diphenols are used to prepare high molecular weight aromatic polycarbonates. Other halogenated polycarbonates have also been obtained by using halogenated monomers as the main polymer building block. Examples of such polycarbonate compositions include those derived from tetrabromobisphenol-A and tetrachlorobisphenol-A monomers as disclosed in U.S. Pat. No. 3,028,365.

Fluorine containing polyarylates are described in a paper published in Izvestiya Akademia Nack SSSr, Seriya Khimicheskaya, No. 9, pp. 1649-1654, September, 1965, (Chemical Abstracts 64, 8321h (1966). Homogeneous and mixed terephthalic, isophthalic, and the like, polyesters of 4,4'-(hexafluoroisopropylidene)diphenol monomer and of 4,4'-[alpha-(trifluoromethyl)-benzylidene]diphenol monomer were synthesized, and it was found that the replacement of CH3 groups on the central carbon atom of the isopropylidene diphenol and the methylene diphenol by CF3 groups leads to a lowering of the softening points of homogeneous and mixed polyesters based thereon. Similar monomers are described in Netherlands patent application No. 6,407,548 filed July 2, 1964, and opened for inspection on Jan. 4, 1965. The Netherlands disclosure relates to a process for the preparation of polycarbonate resin by reacting phosgene with 2,2-bis(p-hydroxphenyl)-1,1,3,3-tetrafluoro-1,3-dichloropropane monomer. The polycarbonate resin was characterized as having very good thermal stability and low vapor permeability. The monomers in the foregoing references were prepared from the corresponding phenol, and in all cases, the positions on the central carbon atom of the diphenol have been substituted with trifluoro- or chlorodifluoromethyl groups or a chlorodifluoro methyl group in combination with a phenyl group.

In U.S. Pat. No. 3,388,097, liquid 4,4'-(1,1,1-trifluoroethylidene)diphenol monomer was made from trifluoroacetaldehyde hydrate and phenol in the presence of anhydrous hydrogen fluoride at 50° C. for 8 hours in a Hastelloy bomb. The liquid product was distilled under reduced pressure at 165°-170° C. and 0.5-0.6 mm. Hg and was obtained in 40% yield. Polyesters were made from these perhaloalkyl bisphenols and specified aromatic acid halides. However, it is noted that the acid catalyst used in making the diphenol is anhydrous hydrogen fluoride; that the reaction is carried out in a "bomb" so as to withstand the considerable autogenous pressure of anhydrous hydrogen fluoride that exceeds 40 to 150 lbs/in.$^2$ at the required reaction temperatures; and that the reaction product distills at 165°-170° C. at reduced pressure. The bisphenols from which the polyesters of U.S. Pat. No. 3,388,097 are made, have the structure:

$$HO-Ar_1-Z-Ar_1-OH \quad (1)$$

wherein Ar1 is para-phenylene, and Z is a divalent radical having the formula:

$$\begin{array}{c} R \\ | \\ -C- \\ | \\ R' \end{array} \quad (2)$$

wherein R and R' may be the same or different and represent perhalogenated lower alkyl groups, fluorine and chlorine being the preferred halogen species, with the provision that R' may represent hydrogen when R represents a perfluorinated lower alkyl group. In U.S. Pat. No. 3,388,097, it is disclosed that these bisphenols or diphenols are prepared by the acid catalyzed condensation of an appropriate halogenated ketone or aldehyde with two molecules of an appropriate phenol. However, as disclosed above, the acid was hydrogen fluoride gas, and there is no suggestion of solid fluorinated diphenols, or of polycarbonates, or of improved flame retardance of the polyesters derived from the fluorinated diphenols or of a non-pressurized or low pressure gaseous acid catalyst system.

Other halogenated diphenols are disclosed in U.S. Pat. No. 2,435,014 and are obtained by condensing two moles of a t,t-octyl-phenol or -naphthol with 1 mole of a polyhalogenated carbonyl compound, and the condensing agents are a mixture of concentrated sulfuric acid-acetic acid and hydrogen chloride-acetic acid. The polyhalogenated carbonyl compounds claimed in making the condensation products in U.S. Pat. No. 2,435,014 are chlorine, bromine or iodine and the examples illustrate chlorine only as a substituent.

SUMMARY OF THE INVENTION

Accordingly, it is the primary object of the present invention to provide a novel process for making very pure fluorinated diphenols.

It is another object of this invention to provide a non-pressurized or low-pressure gaseous acid catalyst system for the preparation of fluorinated diphenols from a phenol and a fluorinated aldehyde compound.

Still another object of this invention is to provide solid fluorinated bisphenols having a fluorinated alkyl or a fluorinated aryl group and a hydrogen atom upon the methylene carbon atom of the bisphenol.

It has now been found that diphenols or bisphenols can be made by mixing a phenol reactant and a fluorinated aldehyde compound in the presence of an acid catalyst selected from the group consisting of anhydrous hydrogen chloride and anhydrous hydrogen bromide at low pressure or at substantially atmospheric pressure.

In accordance with the present invention, there is also provided a fluorinated bisphenol or diphenol having the general formula:

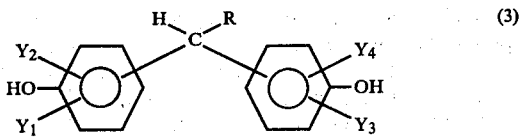

(3)

wherein R is a fluorinated alkyl radical or a fluorinated aryl radical, and $Y_1$, $Y_2$, $Y_3$ and $Y_4$ are each independently selected from the group consisting of hydrogen, alkyl radical having from about 1 to about 4 carbon atoms, chlorine and bromine. In accordance with the present invention, R must be a fluorinated alkyl radical, preferably having from about 1 to about 22 carbon atoms or a fluorinated aryl radical having from 6 to 16 carbon atoms. When R is a fluorinated alkyl radical, R may be a straight chain or a branched fluorinated alkyl radical. In certain preferred embodiments, R is a perfluorinated alkyl or perfluorinated aryl radical.

In the process of the present invention, the phenol reactant is defined as phenol itself as well as alkyl, chlorine and/or bromine derivatives of phenol, and the alkyl group of the substituted phenol may be from about 1 to about 4 carbon atoms.

By the process of the present invention, improvements in the yields of the solid diphenol products are obtained by using anhydrous hydrogen chloride gas or anhydrous hydrogen bromide gas at substantially atmospheric or low pressures, that is, without the use of highly pressurized systems generally required and taught in the prior art when hydrogen fluoride gas is used as the acid catalyst. As used herein, low pressure is defined as a pressure of less than about 30 lbs/in.$^2$. Thus, the process is carried out at pressures ranging from about atmospheric pressure to about 30 lbs/in.$^2$. As used herein, the gaseous system at atmospheric or substantially atmospheric pressure is defined as a non-pressurized gaseous system. Although there is no intention of being limited to a theory, it is believed that the hydrogen chloride gas and the hydrogen bromide gas appear to be more effective and more soluble in the solvent system, and accordingly, the condensation reaction takes place essentially at atmospheric pressure or low pressure without the use of a highly pressurized system or a pressure "bomb".

As used herein, fluorinated diphenol or bisphenol is the fluorinated diphenol of formula (3) with one fluorinated alkyl or fluorinated aryl group attached to the central or methylene carbon atom positioned between the two phenol rings. The terms "central carbon atom" and "methylene carbon atom" are used interchangeably and define the carbon atom positioned between the two phenol rings and having one H and the R attached thereto in formula (3). The fluorinated diphenols have only one fluoroalkyl or one fluoroaryl group upon the central carbon atom, and accordingly, there is conservation of fluorine over many of the prior art fluorinated diphenols which have two fluoroalkyl or fluoroaryl groups thereon. In view of the fact that the fluorine determines the price of the materials, the present invention provides lower cost fluorinated diphenol monomers for the preparation of the flame-retardant polymeric compositions which are made from bisphenol monomers. In accordance with the present invention, it has also been found that substantial improvements in yield are realized when the gaseous hydrogen chloride or hydrogen bromide are used as the acid catalysts at atmospheric or low pressures to make the fluorinated diphenols from a phenol reactant and a fluorinated aldehyde compound. Furthermore, it has also been found by gas chromatographic analyses that the diphenols formed by the novel process of this invention, have very high purity.

DETAILED DESCRIPTION OF THE INVENTION

In certain cases, improved flame retardance is imparted to high molecular weight polymers, such as aromatic polycarbonate resins, by selecting appropriate diphenols to be used with the carbonate precursor in the polymerization reaction. In accordance with the present invention, these diphenols are provided by a novel process in which the diphenols have a fluorinated alkyl or a fluorinated aryl group attached to the central carbon atom, otherwise referred to herein as the methylene carbon atom, positioned between the two phenol rings of the basic bis(hydroxyphenyl)methane structure and derivatives thereof. The central carbon atom is substituted with a hydrogen atom and with a fluorinated alkyl or a fluorinated aryl group as illustrated in general formula (3) above wherein R, $Y_1$, $Y_2$, $Y_3$, $Y_4$ are each defined above. In preferred embodiments, the fluorinated alkyl group represented by R in the diphenol is form about 1 to about 22 carbon atoms and may be partially fluorinated or completely fluorinated (perfluorinated alkyl group). When any one or all of the positions designated by $Y_1$, $Y_2$, $Y_3$ and $Y_4$ are alkyl radicals, in preferred embodiments the alkyl radicals have from about 1 to about 4 carbon atoms. Furthermore, the alkyl radicals represented by R or by $Y_1$, $Y_2$, $Y_3$ and $Y_4$ in the diphenol may be straight chain or branched chains or mixtures thereof. When R represents a fluorinated aryl group, the aromatic substituent may contain from 6 to 16 carbon atoms in which one or all of the hydrogen are replaced by fluorine.

It will be noted that the methylene carbon atom positioned between the two phenol rings has one hydrogen atom, and consequently, there is little or no steric hindrance in the molecule around the central carbon atom. Therefore, all positional isomers of the fluorinated diphenol structures or mixtures thereof can be made in accordance with the present invention from the phenol reactants, including phenol and the phenol derivatives, and the fluorinated aldehyde compound. Thus, while all positional isomers of the fluorinated diphenols of formula (3) are possible, in most cases the isomers are mainly ortho and para, that is, the hydroxy groups are in the ortho and para positions relative to the methylene carbon atom positioned between the two phenol ring structures. In the most preferred embodiments, the isomer is a para, para' isomer when the diphenol monomer is used in conjunction with carbonate and ester precursors and/or other monomers to make polymers or copolymers.

Typical examples of fluorinated diphenols which may be made by the process of the present invention include for example, 4,4'-(2,2,2-trifluorethylidene)diphenol having a melting point of 87° C. to 89° C., 4,4'-(2,2-difluoroethylidene)diphenol, 4,4'-(pentafluoropropylidene)diphenol, 4'-2-(2,2,2-trifluoroethylidene)diphenol, 2,2'-pentafluoropropylidene)diphenol, 4,4'-(perfluorooctylidene)diphenol, 4,4'-(perfluorodecylidene)diphenol, 4,4'-(octafluorobutylidene)diphenol, and the like, including various combinations of fluorinated alkyl groups ranging from about 1 to about 23 carbon atoms, wherein R in the foregoing equation (3) represents from 1 to about 22 carbon atoms; and 4,4'-(pentafluorobenzylidene)bisphenol, 4,4'-(pentafluorobenzylidene)-bis(2,6-dimethylphenol), 4,4'-(pentafluorobenzylidene)-bis(2-methylphenol), and the like including various combinations of fluorinated aryl groups ranging from 6 to 16 carbon atoms, wherein R in equation (3) represents from 6 to 16 carbon atoms. In the foregoing list of diphenols, the complete alkyl group is about 2 to about 23 carbon atoms, and the complete aryl group is about 7 to about 16 carbon atoms when the methylene carbon atom located between the phenol rings is included in the alkyl group. Most of the fluorinated diphenols of the present invention are solids at room temperature and are prepared by combining or mixing the appropriate phenol reactant with the appropriate fluorinated aldehyde compound in the presence of a catalytic amount of an acid catalyst selected from the group consisting of anhydrous hydrogen chloride and anhydrous hydrogen bromide.

The fluorinated diphenols used in the present invention are preferably made from fluorinated aldehydes which are commercially available in the form of the free aldehyde, the aldehyde hydrate, the aldehyde hemiacetal or the acetal. However, any form of the fluorinated aldehyde may be used in accordance with the present invention including the foregoing listed forms, the free form of the aldehyde, the trimer or tetramer form of the aldehyde, the cyclic form of the aldehyde, polymeric forms of the aldehyde and the open-chain form of the aldehyde. Examples of the fluorinated aldehyde compound include perfluoroacetaldehyde, perfluoropropionaldehyde perfluorobutyaldehyde, perfluorooctanaldehyde perfluorobenzaldehyde, or any of the partially or completely fluorinated alkyl aldehydes, straight chain or branched, having from about 2 to about 23 carbon atoms or any of the partially or completely fluorinated aryl aldehydes having from 7 to 17 carbon atoms. The foregoing aldehydes, including mixtures thereof, are reacted with the desired phenol reactants, including herein phenol and phenol derivatives, in an acid catalyzed reaction to form the fluorinated diphenols of the present invention. In preferred embodiments, an excess of the phenol reactant is used in the reaction. The ratio of phenol reactant to aldehyde is not critical as long as there is a sufficient amount of the phenol reactant to react with the fluorinated aldehyde to provide the fluorinated diphenols. The preferred fluorinated aldehyde compounds are generally the perfluorinated aldehyde compounds.

Any appropriate phenol, substituted phenol or phenol derivative may be used in the reaction mixture to make the diphenols and are designated herein as phenols, phenol reactants or phenol compounds. The preferred phenol reactant is generally phenol itself. Other phenols include, for example, o-cresol, 2,6-xylenol, 6-chloroorthocresol, orthocholorophenol or any phenol compound substituted with alkyl radicals having preferably from about 1 to about 4 carbon atoms, chlorine or bromine and having at least one replaceable hydrogen on the ring.

The acid catalysts used in the process of the present invention are critical and include only gaseous hydrogen chloride and gaseous hydrogen bromide used at substantially atomspheric pressure or low pressure (at or less than about 30 lbs/in.$^2$). Pressure, pressure bombs and pressure vessels are not necessary in the process of the present invention, and the reaction process steps of the present invention can be carried out at even atmospheric pressure without the necessity of pressure or pressurized vessels. Gaseous hydrogen fluoride acid is disclosed as acid catalyst in U.S. Pat. No. 3,388,097, however, it requires a pressure bomb capable of withstanding at least 200 lbs/in.$^2$ pressure and exceptionally long periods of time to catalyze the reaction under relative rigorous conditions, and it appears that oils or liquids of unknown composition in low yield rather than solid fluorinated diphenols in high yield are obtained from the reaction of the phenol compound and certain of the fluorinated compounds when anhydrous hydrogen fluoride is used under pressure as the acid catalyst by the prior art technique.

The solid fluorinated diphenols of the present invention may be made by mixing the phenol reactant and the fluorinated aldehyde compound in the presence of gaseous hydrogen chloride and/or hydrogen bromide acid catalyst in any desired manner at atmospheric or substantially atmospheric pressures or at low pressures not exceeding about 30 lbs/in.$^2$. For example, the molten phenol may be saturated with the gaseous HCl or HBr, and the fluorinated aldehyde compound may be gradually introduced into the non-pressurized reaction vessel containing the molten phenol.

Although external heat is not required in the reaction of the phenol compound and the fluorinated aldehyde compound to produce the solid fluorinated diphenols in the presence of the gaseous HCl or HBr acid catalyst, it is preferred to heat the reaction mixture above ambient up to about 200° C., depending upon the nature of the acid catalyst. Optimum temperatures are generally about 40° C. to about 140° C. The acid catalyst material is present in a catalytic amount, however, the amount of acid is generally an amount which saturates the phenol and/or the reaction mixture in which water and/or alcohol are formed during the reaction. In preferred embodiments, the acid catalysts are anhydrous so that they will not introduce water into the reaction mixture, although it is understood that water and/or alcohol are formed in the condensation reaction leading to diphenols, depending upon the nature of the aldehyde precursor employed.

It is also possible to use co-catalysts, such as, mercaptans and other sulfhydryl-containing compounds, with the acid catalyst to speed up the proton-catalyzed reaction. Optional steps include separation of the isomers, for example, by recrystallization, by distillation or by solvent separation techniques to separate the o,o' and o,p' from the p,p' isomers.

The chlorination or bromination of the fluorinated diphenol may be carried out before the diphenol is formed or after the diphenol is formed by conventional halogenation techniques when the chlorine or bromine derivatives of the fluorinated bisphenol are desired. For example, the phenol compound or compounds used to make the diphenols may contain the chlorine or bromine radicals or mixtures thereof before reaction with the appropriate fluorinated aldehyde, or the bromine or chlorine radicals or mixtures thereof may be placed upon the fluorinated diphenol after it has been synthesized from the phenol compound and the appropriate fluorinated aldehyde. When alkyl derivatives of the fluorinated diphenols are desired, they are best prepared from the corresponding alkylphenol precursors, such as, o-cresol, 2,6-xylenol, o-isopropylphenol, o-tertiarybutylphenol, 2-chloro-6-methylphenol and the like.

The following specific examples describe the novel diphenol compositions and the novel process of making the diphenol compositions of the present invention. They are intended for illustrative purposes only and should not be construed as a limitation.

EXAMPLE 1

Preparation of 4,4'-(1H-1,1-perfluorooctylidene)bisphenol

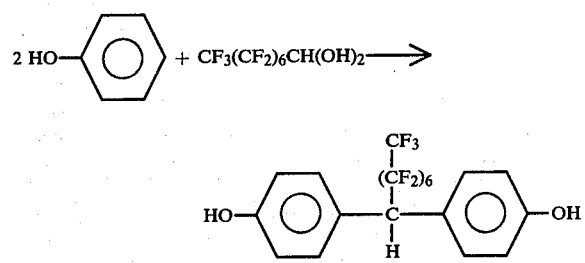

Into a one liter three-necked flask equipped with an electric stirrer, gas inlet tube reaching below the surface of the reaction mixture, thermometer and reflux condenser are placed 380 g of phenol (4 moles) and 83.2 g (0.2 mole) of perfluorooctanaldehyde hydrate. The mixture is heated to 60° C., when anhydrous hydrochloric acid gas is introduced with good stirring, until saturated, then, at lower rate so as to maintain an excess of it continuously in the reaction mixture at that temperature. The progress of the reaction is followed by gas chromatography, which indicated the formation of very little of the o,o'- and o,p', but mostly of the p,p'-isomer. The warm slurry was filtered, the filter cake rinsed twice with cyclohexane and recrystallized from methylene chloride. The pure white crystals, which had the correct analytical composition data for $C_{20}H_{11}F_{15}O_2$, were found to be 99.5% pure by gas chromatography and to have a sharp melting point of 138°–139° C. The p,p'-isomeric structure was confirmed by proton nmr, which displayed the AB quadruplet characteristic for paradisubstituted benzene rings.

EXAMPLE 2

Preparation of 4,4'-(1H-1,1-perfluorobutylidene)bisphenol

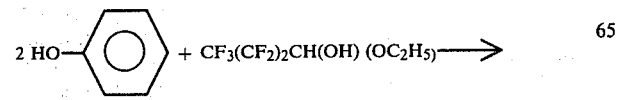

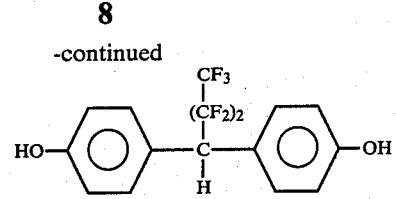

The procedure of Example 1 was repeated, except that the perfluorooctanaldehyde hydrate was replaced with 48.8 g (0.2 mole) of perfluorobutyraldehyde ethylhemiacetal. When gas chromatography indicated no change in the composition of the reaction mixture, the excess phenol was removed by distillation under water aspirator vacuum to yield a residue of 62 g, which is 84% of the theoretical amount and which by gas chromatographic analyses contained 93.4% of the p,p'- and 5.2% of the o,p'-isomer. Recrystallization from benzene yielded white crystals of 99.4% purity, that melted sharply at 117°–118° C. and were shown to be the p,p'-isomer by the characteristic AB quadruplet in the nmr.

EXAMPLE 3

Preparation of 4,4'-(1H-trifluoroethylidene)bis(2-methylphenol)

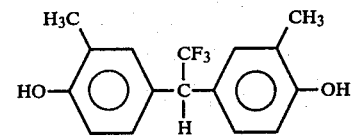

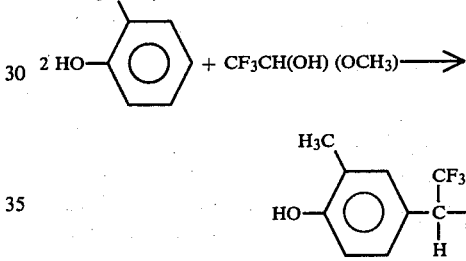

Repeating the procedure of Example 1, but replacing the phenol with 432 g (4.0 moles) of o-cresol and the perfluorooctanaldehyde hydrate with 26.0 g (0.2 mole) of trifluoroacetaldehyde methyl hemiacetal, yielded after stripping-off the excess o-cresol in vacuum at the end of the reaction a pale yellow residue that was recrystallized from a mixture of cyclohexane benzene. The white crystals were obtained in 94% yield, had a melting point of 58°–60° C. and were 99.6% pure by gas chromatographic analysis.

EXAMPLE 4

Preparation of 4,4'-(1H-trifluoroethylidene)bis(2,6-dimethylphenol)

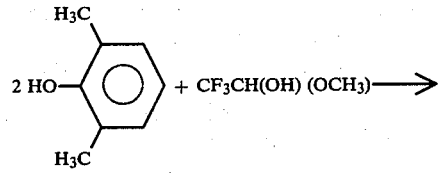

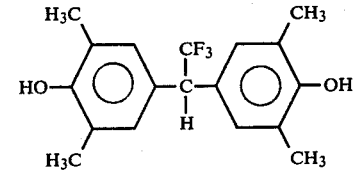

Repeating the procedure of Example 3 with 488 g (4 moles) of 2,6-xylenol in place of the o-cresol, yielded title compound in 92% yield, which after recrystallization from cyclohexane melted sharply at 83° to 84.5° C. and were 99.1% pure by gas chromatographic analysis.

EXAMPLE 5

Preparation of 4,4'-(1H-trifluoroethylidene)bisphenol

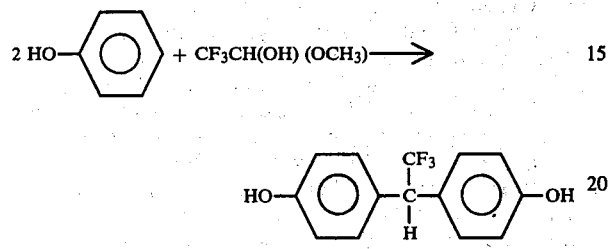

When the procedure of Example 3 was repeated with 380 g (4 moles) of phenol replacing the o-cresol, to yield title compound in 93.5% yield, that after recrystallization from cyclohexane-benzene melted at 87° to 89° C. and was shown to be the 99.8% pure p,p'-isomer by the AB quadruplet in its proton nmr spectrum.

EXAMPLE 6

Preparation of 4,4'-(pentafluorobenzylidene)bisphenol

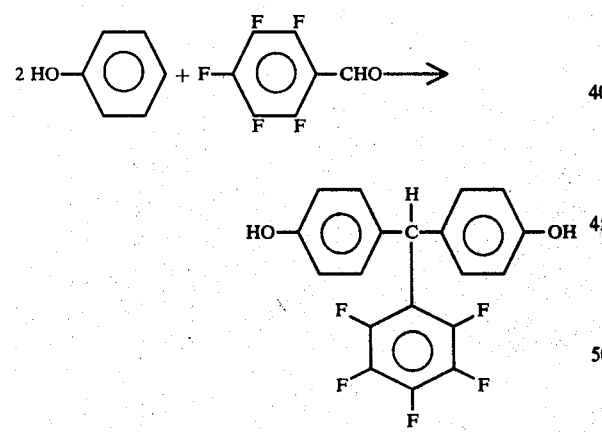

The procedure of Example 1 was repeated, except that the perfluorooctanaldehyde hydrate was replaced with 39.2 g (0.2 mole) of pentafluorobenzaldehyde and the gaseous hydrochloric acid catalyst with gaseous hydrobromic acid. After the distillation of the excess phenol, the residue showed by gas chromatography the presence of 12.6% of 2,2'-(pentafluorobenzylidene)bisphenol, 37.0% of 2,4'-(pentafluorobenzylidene)bisphenol and 50.4% of 4,4'-(pentafluorobenzylidene)bisphenol. The latter was isolated by recrystallization from cyclohexane.

EXAMPLE 7

Preparation of 4,4'-(pentafluorobenzylidene)bis(2,6-dimethylphenol)

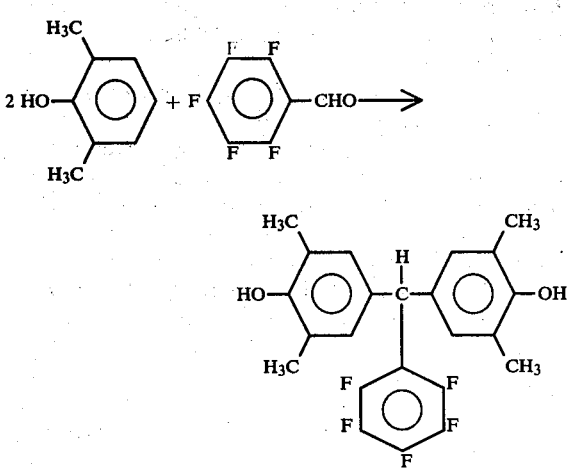

The procedure of Example 4 was exactly repeated, except that the trifluoroacetaldehyde methyl hemiacetal was replaced with 39.2 g (0.2 mole) of pentafluorobenzaldehyde. After 2 hours of contacting the reaction mixture with hydrochloric acid gas, the excess xylenol was removed by vacuum distillation, and the bright yellow product, that was obtained in 98% yield, was recrystallized from cyclohexane. The sulfur-colored crystals melted sharply at 157° to 159° C. and were shown to be 99.3% pure by gas chromatography.

EXAMPLE 8

Preparation of 4,4'-(pentafluorobenzylidene)bis(2-methylphenol)

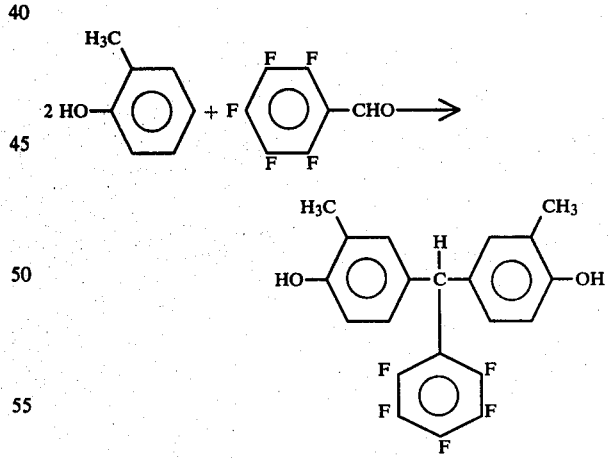

Repeating the procedure of Example 3, but replacing trifluoroacetaldehyde methyl hemiacetal with 39.2 g (0.2 mole) of pentafluorobenzaldehyde, yielded the following composition: 2,2'-(pentafluorobenzylidene)bis(6-methylphenol) 4.5%; 2,4'-(pentafluorobenzylidene)6,2'-dimethylbisphenol) 35.7% and 4,4'-(pentafluorobenzylidene) bis(2-methylphenol) 59.8%. Recrystallization from cyclohexane yielded pale yellow crystals of the 4,4'-isomer, which melted at 111° to 113° C. and were of 95.2% purity.

While the invention has been described with respect to preferred embodiments, it will be apparent that certain modifications and changes can be made without departing from the spirit and scope of the invention and, therefore, it is intended that the foregoing disclosure be limited only by the claims appended hereto.

What is claimed is:

1. An improved method of making bisphenols having a fluorinated alkyl of 1 to about 22 carbon atoms or fluorinated aryl group of 6 to about 16 carbon atoms and a hydrogen atom upon the methylene carbon atom of the bisphenol comprising mixing at low pressure or up to about 30 lbs/in. sq. a phenol reactant and a fluorinated alkyl of 2 to about 23 carbon atoms or aryl of 7 to about 17 carbon atoms aldehyde compound in the presence of an acid catalyst selected from the group consisting of anhydrous hydrogen chloride and anhydrous hydrogen bromide.

2. The method of claim 1, further comprising heating the mixture at a temperature ranging from ambient to about 200° C.

3. The method of claim 1, wherein the phenol is substituted with hydrogen, chlorine atoms, bromine atoms, alkyl radicals or mixtures thereof.

4. The method of claim 3, wherein the alkyl radicals have from about 1 to about 4 carbon atoms.

5. The method of claim 1, comprising mixing about 2 moles of the phenol for about every 1 mole of the fluorinated aldehyde compound.

6. The method of claim 1, wherein the fluorinated aldehyde compound is in the form selected from the group consisting of the free form of the aldehyde, the hydrate, the hemiacetal form, the acetal form, the trimer form, the tetramer form, the cyclic form and the open chain form.

7. The method of claim 1, wherein the fluorinated aldehyde compound is perfluorinated.

8. The method of claims 1, 6 or 7, wherein the fluorinated aldehyde compound is a fluorinated alkyl aldehyde having from about 2 to about 23 carbon atoms.

9. The method of claims 1, 6 or 7 wherein the fluorinated aldehyde compound is a fluorinated aryl aldehyde having from about 7 to about 17 carbon atoms.

10. The method of claim 1 wherein the phenol reactant is selected from the group consisting of phenol, alkyl derivatives of phenol wherein the alkyl group has from about 1 to about 4 carbon atoms, phenol substituted with chlorine and phenol substituted with bromine.

* * * * *